US00PP20277P2

(12) United States Plant Patent
Feng

(10) Patent No.: US PP20,277 P2
(45) Date of Patent: Sep. 8, 2009

(54) ***PHALAENOPSIS* PLANT NAMED 'SOGO F1982'**

(50) Latin Name: ***Phalaenopsis* Orchid**
Varietal Denomination: SOGO F1982

(76) Inventor: Chiang-Kuei Feng, No. 1-1, Chenggong Xincun, Jiyang Village, Meinong Town, Kaohsiung County (TW)

( * ) Notice: Subject to any disclaimer, the term of this patent is extended or adjusted under 35 U.S.C. 154(b) by 0 days.

(21) Appl. No.: 12/151,458

(22) Filed: May 7, 2008

(51) Int. Cl.
*A01H 5/00* (2006.01)

(52) U.S. Cl. ..... Plt./311
(58) Field of Classification Search ..... Plt./311
See application file for complete search history.

*Primary Examiner*—Annette H Para
(74) *Attorney, Agent, or Firm*—Frenkel & Associates, P.C.

(57) ABSTRACT

A new and distinct cultivar of *Phalaenopsis* plant named 'SOGO F1982', comprises its flowers of abundant purple dapple overlaid with yellow toward pink base and the pink with white labellum, freely flowering habit, upright, freely branching and sturdy flowering stems, and the excellent post-production longevity.

2 Drawing Sheets

FIELD OF THE INVENTION

Botanical classification/cultivar designation: *Phalaenopsis* Orchid cultivar SOGO F1982.

BACKGROUND OF THE INVENTION

The present invention comprises a new and distinct cultivar of *Phalaenopsis* Orchid, a bigeneric hybrid of *Phalaenopsis*× *Phalaenopsis* of the family Orchidaceae, and hereinafter referred to as the cultivar name, SOGO F1982. The genus *Phalaenopsis* is a member of the family Orchidaceae.

*Phalaenopsis* comprise a group of bigeneric hybrids generally intermediate in character between the parent genera, which are suitable for cultivation in the home or greenhouse. The parent genera of *Phalaenopsis* are predominantly epiphytic or rock dwelling, and are native to tropical Asia, Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

*Phalaenopsis* orchid, often referred to 'Moth Orchids' in the horticultural trade, are frequently used to furnish cut flowers for the florist trade, or sold as flowering potted plants for home or interiorscape.

*Phalaenopsis* produce upright racemes, often with many showy flowers, which open in succession beginning with the lowermost. The flowers possess three sepals, and three petals, the lateral ones being alike. The lowermost petal, called the labellum, is three lobed and is often more brightly colored than other flower segments. Flower colors are frequently various shades of pink, white and yellow.

*Phalaenopsis* orchids are typically propagated from seeds. However, *Phalaenopsis* is capable of being asexually reproduced from offshoots, which frequently arise from the lower bracts of the inflorescence. The resulting plants are detached from the mother plant and may be planted in a suitable substrate.

'SOGO F1982' is a product of a planned breeding program conducted by the inventor in Kaohsiung County, Taiwan, R.O.C. The objective of the breeding program is to create new uniform pot-type *Phalaenopsis* Orchid cultivars having attractive flower coloration. The inventor has addressed himself to the Orchid breeding since 1985.

'SOGO F1982' was discovered by the inventor from within the progeny of a cross-pollination of one *Phalaenopsis* Orchid, Phal. 'Brother Peterstar' and one *Phalaenopsis* Orchid, Phal. 'Brother Sara Gold' on February 1999, in a controlled environment in Kaohsiung County, Taiwan, R.O.C.

Asexual propagation by tissue culture in a laboratory in Pingdong County, Taiwan, R.O.C. has been used to increase the number of plants for evaluation and has demonstrated in a controlled environment in Kaohsiung County, Taiwan, R.O.C. that the unique combination of characteristics as herein disclosed for the new *Phalaenopsis* Orchid are firmly fixed and are retained through successive generations of asexual reproduction.

SUMMARY OF THE INVENTION

The following traits have been repeatedly observed and are determined to be basic characteristics of 'SOGO F1982' which in combination distinguish this *Phalaenopsis* Orchid as a new and distinct cultivar:

1. Abundant purple dapple overlaid with yellow toward pink base and the pink with white colored labellum.
2. Freely flowering habit.
3. Upright, freely branching and sturdy flowering stems.
4. Excellent postproduction longevity.

Plants of 'SOGO F1982' differ primarily from plants of the parent cultivars in flower color. The main color of the petals of Phal. Brother Peterstar is RHS 21A and the pattern color thereof is RHS 34A. The main color of the petals of Phal. Brother Sara Gold is RHS 21C and the pattern color thereof is RHS 34A.

Currently, there is no commercial cultivar to which 'SOGO F1982' can be meaningfully compared.

BRIEF DESCRIPTION OF THE DRAWINGS

The accompanied photographic illustrations show typical plant and flower characteristics of 'SOGO F1982' with colors being as true as possible with illustrations of this type.

DETAILED DESCRIPTION OF THE PREFERRED EMBODIMENTS

Figure 1:
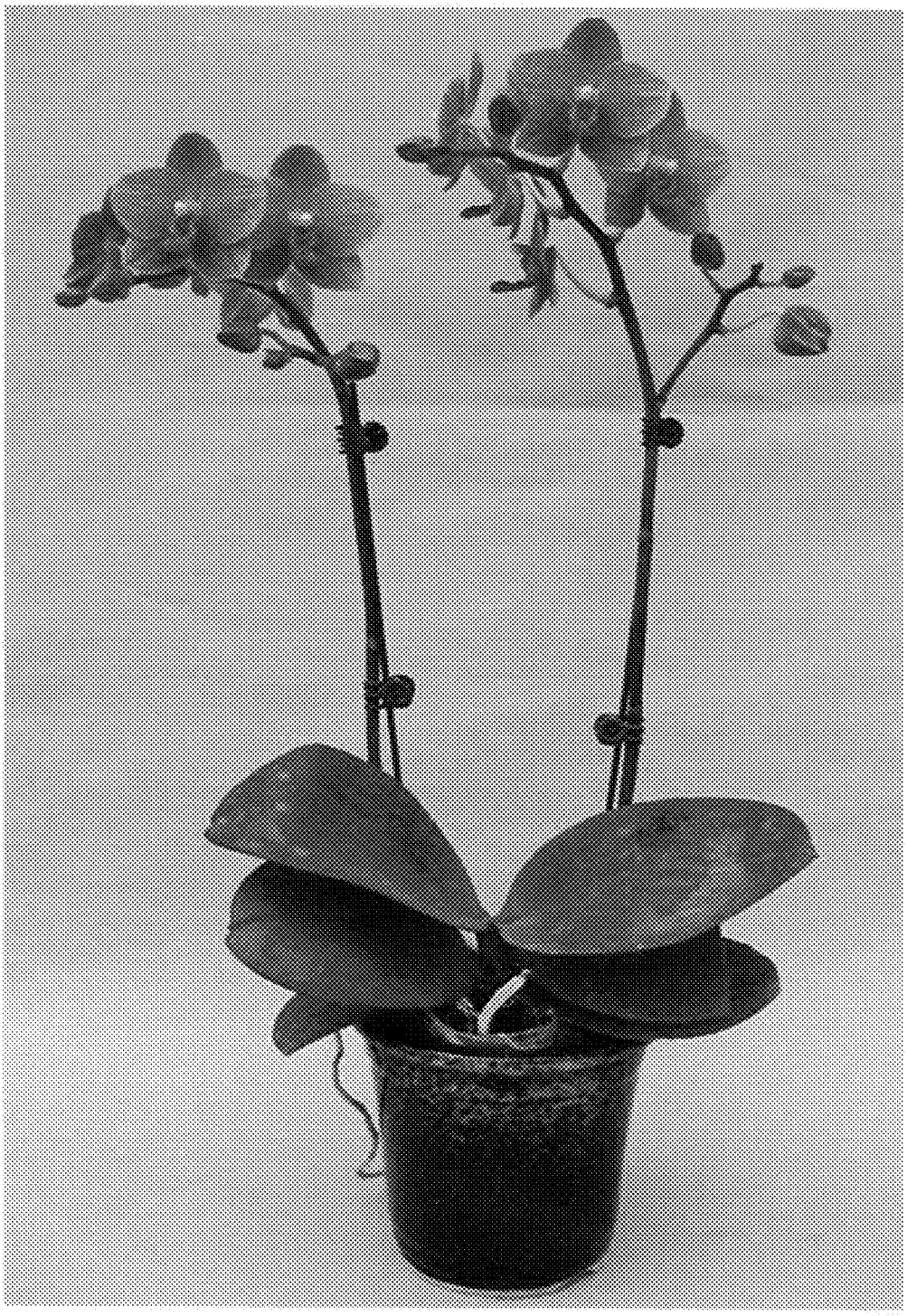
FIG. 1 is a side view of a plant of 'SOGO F1982' flowering in the pot of 13 cm.
Figure 2:
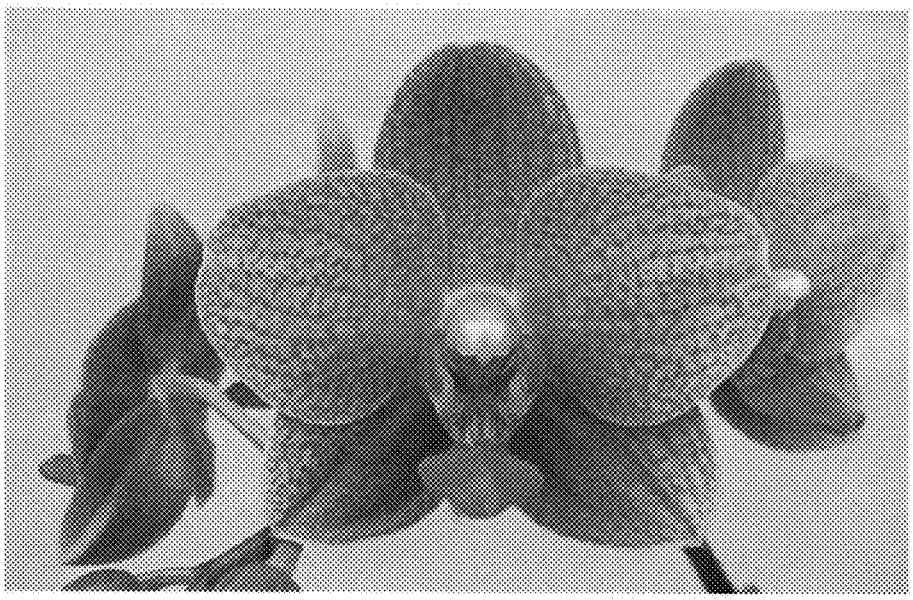
FIG. 2 is a close-up view showing the characteristics of the flower.
Figure 3:
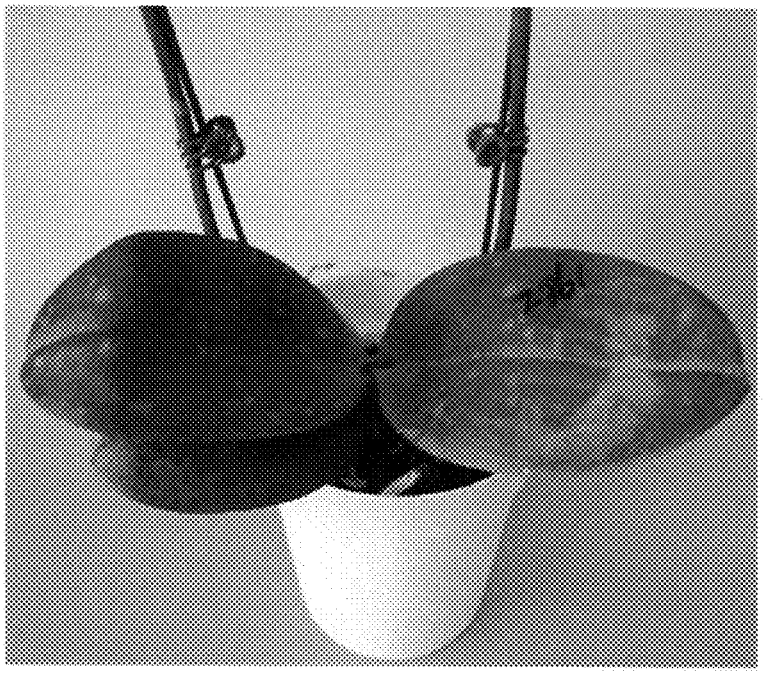
FIG. 3 is a close-up view showing the characteristics of the leaf.

'SOGO F1982' has not been observed under all possible environmental conditions. The phenotype may vary significantly with variations in environment such as temperature, light intensity, fertilization and day length without any change in the genotype.

The observations and measurements describe plants grown in Kaohsiung County, Taiwan, R.O.C. under the conditions, which approximate those generally used in commercial practice.

In the following description, color references are made to The Royal Horticultural Society (R.H.S.) Color Chart.

Plants used for the aforementioned photographs and the following detailed botanical description were 18 months in maturity and grown in the pots of 13 cm, in a controlled greenhouse with day-night temperature around 25–18 degree Celsius, and light intensity between 15,000~20,000 lux natural light, in Kaohsiung County, Taiwan, R.O.C.

Origin: Seedling from a cross of the selected *Phalaenopsis* orchids as described above.

Classification: *Phalaenopsis* hybrid cv. 'SOGO F1982'.

Propagation: Asexual propagation by tissue culture.

Plant description:

*Plant height.*—Soil level to top of foliar plane is about 10 to 15 cm.

*Plant height.*—Soil level to top of inflorescences is about 35 to 45 cm.

*Plant diameter.*—Is about 20 to 25 cm.

*Growth habit.*—Compact, small, dark-green leaves and a relatively short raceme.

*Flowers per stem.*—Approximately 5 to 15.

Foliage description:

*Quantity.*—Approximately 6 to 8 leaves are produced before flowering.

*Size of leaf.*—10 to 15 cm long and 7 to 9 cm wide.

*Shape.*—The leaf blade is short and elliptic with a cuneate base and an obtuse tip. The leaf blade is leathery and thick. The middle vein protrudes, while the other veins are not visible in the thick leaf blade.

*Attitude.*—Horizontal and on two sides parallel.

*Color.*—Upper surface: Dark-green, RHS 137B. Lower surface: Light-green, RHS 137C.

Inflorescence description:

*Flower type and habit.*—Single zygomorphic flowers arranged in racemes. Flowers are roughly pentagonal in shape. Flowering stems upright, freely branching and sturdy. Plants freely flowering; plants typically produce one to three branched flowering stems with at least 4 to 12 flowers each.

*Fragrance.*—No fragrance.

*Natural flowering season.*—From February to April in the southern part of Taiwan. The flower spikes can be induced under the controlled environment, of which day-night temperature at 25–18 degree C. for 2 weeks.

*Post-production longevity.*—Plants of 'SOGO F1982' maintain good leaf and flower substance for about three to six months on the plant under interior environmental conditions. Lastingness of cut flowers has not been observed.

*Inflorescence length.*—About 18 to 23 cm.

*Inflorescence diameter.*—About 35 to 40 cm.

*General impressions of petals and sepals.*—Horizontal elliptical in shape, about 5.3 cm of flower width in front view.

*Sepals.*—There are 3 sepals which are fleshy and glabrous in texture, with straight margins and in elliptical shape, about 2.6 cm in length and 1.9 cm in diameter. The main color of dorsal sepal is RHS N144B, the pattern color of dorsal sepal is 60C. The main color of lateral sepals is RHS N144B, the pattern color of lateral sepal is 59A.

*Petals.*—There are 2 open petals which are fleshy and glabrous in texture, with margins weakly undulate and in elliptical shape, about 2.5 cm in length and 2.3 cm in diameter. The main color of petals is RHS 7A, the pattern color of petals is 60C.

*Labellum* (*lip*).—The lip whiskers are absent, shape of apical lobe is ovate, approximately 1.7 cm long and 1.2 cm wide. The base color of apical lobe is RHS 59B, the tip color of apical lobe is RHS N74A.

*Peduncles.*—Length about 35 to 45 cm, diameter about 9 mm, upright, strong and sturdy, with smooth and glabrous texture. Color is RHS 137C.

*Pedicels.*—Length about 3.6 cm, diameter about 3 mm. Aspect about 60.degree from vertical. Strong, with a texture of smooth and glabrous. Color RHS 145D, towards the base, overlaid with RHS 144A.

Reproductive organs: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*—Approximately 10 mm long and 5 mm wide, RHS N78C.

*Pollinia.*—Two, about 1 mm oval masses of pollen present, RHS 17A.

*Ovary.*—5 to 7 mm long and 2.4 mm in diameter, RHS 75B. Roots: Fleshy, approximately 5 mm wide and green, RHS 191B.

Plant disease resistance/susceptibility: No specific resistance or susceptibility observed.

General observations: *Phalaenopsis* 'SOGO F1982' produces two or more inflorescence with flowers having sepals and petals in the color of abundant purple dapple overlaid with yellow toward pink base. A pink white labellum. The inflorescence is strong, erect and sturdy, relatively short, and easily packaged for shipping. The plant grows very quickly to marketable size. 'SOGO F1982' can be economically propagated via tissue culture.

What is claimed is:

1. A new and distinct cultivar of *Phalaenopsis* orchid plant named 'SOGO F1982' as illustrated and described.

* * * * *